(12) United States Patent
Davis et al.

(10) Patent No.: US 9,234,246 B1
(45) Date of Patent: Jan. 12, 2016

(54) DECENTRALIZED ELECTRICAL LOAD SHEDDING

(75) Inventors: Benjamin Davis, San Francisco, CA (US); Alexander Nelson Brooks, Pasadena, CA (US)

(73) Assignee: Google Inc., Mountain View, CA (US)

( * ) Notice: Subject to any disclaimer, the term of this patent is extended or adjusted under 35 U.S.C. 154(b) by 852 days.

(21) Appl. No.: 13/444,694

(22) Filed: Apr. 11, 2012

(51) Int. Cl.
*H02J 3/14* (2006.01)
*C12Q 1/68* (2006.01)

(52) U.S. Cl.
CPC .................................. *C12Q 1/6886* (2013.01)

(58) Field of Classification Search
USPC ................................ 700/22; 307/35; 705/412
See application file for complete search history.

(56) References Cited

U.S. PATENT DOCUMENTS

| | | | | |
|---|---|---|---|---|
| 4,319,329 A * | 3/1982 | Girgis | .................... | G01R 23/02 324/76.21 |
| 7,149,499 B1 * | 12/2006 | Oran | .................... | H04M 11/04 455/404.1 |
| 7,582,986 B2 * | 9/2009 | Folkers | .................... | H02J 3/14 307/39 |
| 8,073,573 B2 * | 12/2011 | Chassin | .................... | H02J 3/14 700/286 |
| 8,627,689 B2 * | 1/2014 | Finch et al. | .................... | 68/12.12 |
| 2004/0254654 A1 * | 12/2004 | Donnelly | .................... | H02J 3/14 700/22 |
| 2004/0254688 A1 * | 12/2004 | Chassin | .................... | H02J 3/14 700/295 |
| 2006/0195230 A1 * | 8/2006 | Lenarduzzi | .................... | G06Q 50/06 700/292 |
| 2006/0235574 A1 * | 10/2006 | Lapinski | .................... | H02J 3/0086 700/286 |
| 2007/0222294 A1 * | 9/2007 | Tsukida | .................... | H02J 3/14 307/29 |
| 2009/0009349 A1 * | 1/2009 | Wiszniewski | .................... | H02J 3/24 340/635 |
| 2009/0012916 A1 * | 1/2009 | Barnett | .................... | G06Q 50/06 705/412 |
| 2009/0299540 A1 * | 12/2009 | Abi-Samra | .................... | H02J 3/14 700/295 |
| 2010/0244563 A1 * | 9/2010 | Fleck | .................... | H02J 3/14 307/35 |
| 2011/0213739 A1 * | 9/2011 | Benitez | .................... | G01D 4/004 706/12 |

OTHER PUBLICATIONS

Mozina, C., "Undervoltage Load Shedding," Power Systems Conference: Advanced Metering, Protection, Control, Communication, and Distributed Resources, 2007. PSC 2007, Mar. 13-16, 2007,16 pages, [Online] [Retrieved on Aug. 9, 2012] Retrieved from the Internet<URL:http://www.beckwithelectric.com/docs/tech-papers/undervoltage_loadshedding.pdf>.

* cited by examiner

*Primary Examiner* — Jared Fureman
*Assistant Examiner* — Emmanuel R Dominique
(74) *Attorney, Agent, or Firm* — Fish & Richardson P.C.

(57) ABSTRACT

A decentralized load shedding device turns off a load in response to determining that an electric grid is approaching its maximum operating point. By turning off the load, demand on the electric grid is minimized thereby reducing the likelihood of blackouts. The device may be coupled to the load or may be incorporated into the load in one embodiment.

10 Claims, 4 Drawing Sheets

DECENTRALIZED ELECTRICAL LOAD SHEDDING

BACKGROUND

1. Field of Art

The present disclosure generally relates to decentralized electrical load shedding of an electric grid.

2. Description of Related Art

A blackout may be a short-term or long-term loss of electrical power to a geographical area. Blackouts may occur when the demand for electricity exceeds the power supply available on an electric grid. A centralized demand response by utility companies is one solution to prevent or at least alleviate the occurrence of blackouts. Particularly, a utility company may direct electricity to a geographical area that is exceeding the supply for the area from another geographical area with excess supply.

However, a centralized demand response requires the development of additional infrastructure to support the centralized demand response. The infrastructure may include a central communications system, new electrical meters, communication wires and protocols, and software to manage the demand response. Therefore, the additional infrastructure has high development costs. The additional infrastructure further requires involvement by the government to enforce and regulate the centralized demand response. As a result, the centralized demand response is not a feasible short-term solution to prevent or minimize the occurrence of blackouts.

SUMMARY

When an electric grid reaches a threshold of its maximum operating capacity, the electric grid may lower its operating frequency from a first frequency to a lower second frequency to account for the additional demand on the electric grid. The frequency is lowered by an amount that does not cause problems with most electrical devices (e.g., home appliances). In one embodiment, a load shedding device senses (i.e., identifies) the lower operating frequency of the electric grid that signifies that the electrical grid is approaching its maximum capacity. In response, the device sends a signal instructing the load, such as an electric appliance, to turn off. Thus, if a number of load shedding devices turn off in response to the electrical grid approaching its maximum capacity, the demand on the electric grid is alleviated.

If each of a plurality of loads is coupled to a load shedding device or if each load is incorporated with a load shedding device, the demand on the electric grid is minimized when the load shedding devices instruct the loads to turn off in response to sensing that the electric grid is approaching its maximum capacity. Turning off the loads aids in the prevention of blackouts since the demand on the electric grid is reduced.

Furthermore, the load shedding devices do not require a centralized system to operate since no additional infrastructure is needed for people to use the devices. Therefore, people are not subjected to any additional costs to implement the decentralized load shedding provided by the devices.

The features and advantages described in the specification are not all inclusive and, in particular, many additional features and advantages will be apparent to one of ordinary skill in the art in view of the drawings, specification, and claims. Moreover, it should be noted that the language used in the specification has been principally selected for readability and instructional purposes, and may not have been selected to delineate or circumscribe the inventive subject matter.

The figures depict various embodiments for purposes of illustration only. One skilled in the art will readily recognize from the following description that alternative embodiments of the structures and methods illustrated herein may be employed without departing from the principles described herein.

DETAILED DESCRIPTION

System Architecture

An electric grid supplies electrical power to loads. The term "load" may refer to a particular power drawing electrical component such as air conditioners, televisions, computers, refrigerators, etc. Generally, an electric grid comprises one or more power plants of rotating machinery that are operated by a supplier, such as an entity owning the power plants. The power plants generate the electricity that is supplied by the electric grid. A power plant may be, for example, based on a non-renewable energy source such as a fossil fueled power plant or a nuclear power plant. Alternatively, a power plant may be, for example, based on a renewable energy source such as a solar thermal electric plant, a solar photovoltaic power plant, a hydroelectric power plant, or a wind turbine.

The frequency of operation of the electric grid indicates whether the operating point limits of the electric grid is being approached. More specifically, the relative change in the frequency of operation and the duration of the change in frequency indicates whether the operating point limits of the electric grid is being approached. For example, the frequency of operation of the electric grid reducing by 0.1 Hz (i.e., a relative threshold frequency) and being maintained for five minutes (i.e., a threshold amount of time) signifies the limits of the electric grid is being approached. Relying on the relative change of frequency and the duration of the frequency change helps prevent false triggering of load shedding devices due to the load shedding devices having a drift in measurement or drift in timing accuracy that renders the load shedding devices incapable of measuring the absolute accuracy or due to momentary spikes in measured frequency from electronic noise.

Figure 1A:
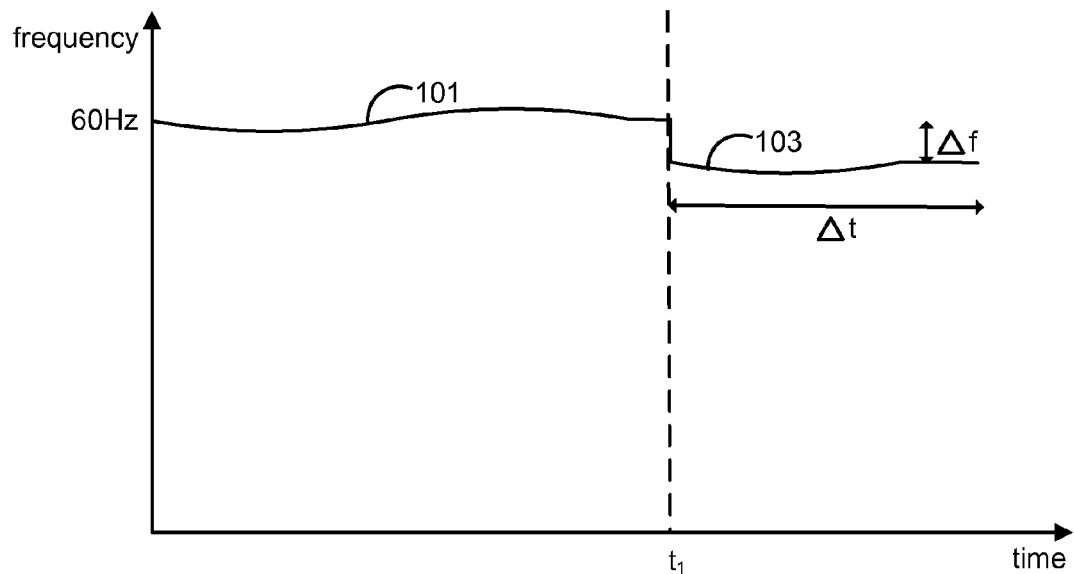
FIG. 1A and FIG. 1B respectively illustrate a graph of the operating frequency of an electric grid with respect to time and a graph of the load of the electric grid with respect to time, according to one embodiment.
Figure 1B:
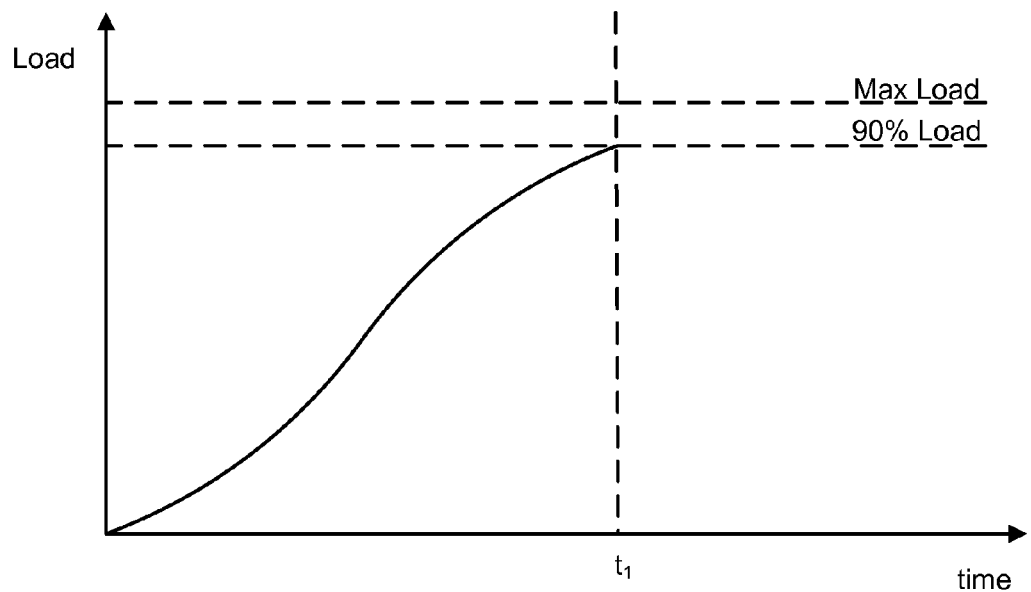

FIG. 1A illustrates one embodiment of the operating frequency of an electric grid with respect to time. FIG. 1B illustrates one embodiment of the demand on the electric grid with respect to time. As shown in FIG. 1A, the grid frequency prior to time $t_1$ does not vary significantly from an operating point frequency (e.g., 60 Hz) 101. The steady operating frequency 101 of the electric grid prior to time $t_1$ in FIG. 1A coincides with the demand on the electric grid being less than a threshold percentage of the maximum load that the grid can support as shown in FIG. 1B. In one embodiment, the threshold percentage is 90% of maximum load, but other thresholds may be used.

Responsive to the demand on the electric grid reaching the threshold percentage of maximum load at time $t_1$ as shown in FIG. 1B, the operating frequency of the electric grid is lowered (i.e., stepped down) to a lower operating frequency 103 at time $t_1$ as shown in FIG. 1A. The frequency is lowered by an amount that does not cause problems with most electrical devices (e.g., home appliances). In one embodiment, the operating frequency of the electric grid may be lowered by 0.1 Hz (e.g., $\Delta f$) however other operating frequencies may be used. Specifically, an operator of the grid may artificially induce a lower operating point for a duration of time (e.g., $\Delta t$) of the electric grid in response to the electric grid reaching the threshold percentage of the maximum load. In one embodiment, the lower operating frequency of the electric grid for the duration of time signifies that the electric grid is approaching is maximum capacity.

In one embodiment, the operating frequency of the electric grid may be encoded with information describing the geographic region(s) which are affected by the lower operating point of the electric grid. The information may also describe which types of electrical devices are affected by the lower operating point of the electric grid. In one embodiment, Huffman coding may be used to encode the operating frequency with the information. Other coding schemes may be used in different embodiments. As will be further described below, the encoded information may be used in addition to the lower operating frequency of the electric grid to signify to the load shedding devices whether to turn off their loads.

Figure 1D:
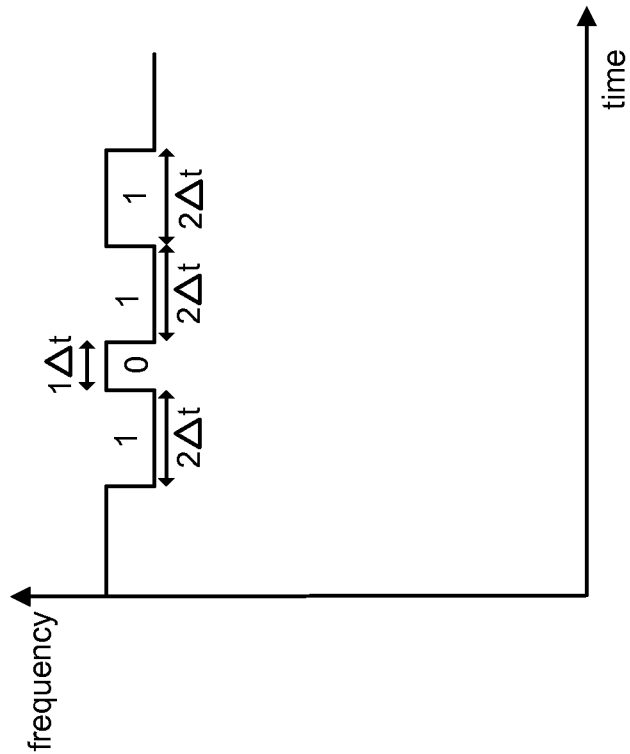
FIG. 1C and FIG. 1D illustrate encoding schemes of the operating frequency of the electric grid according to one embodiment.
Figure 1C:
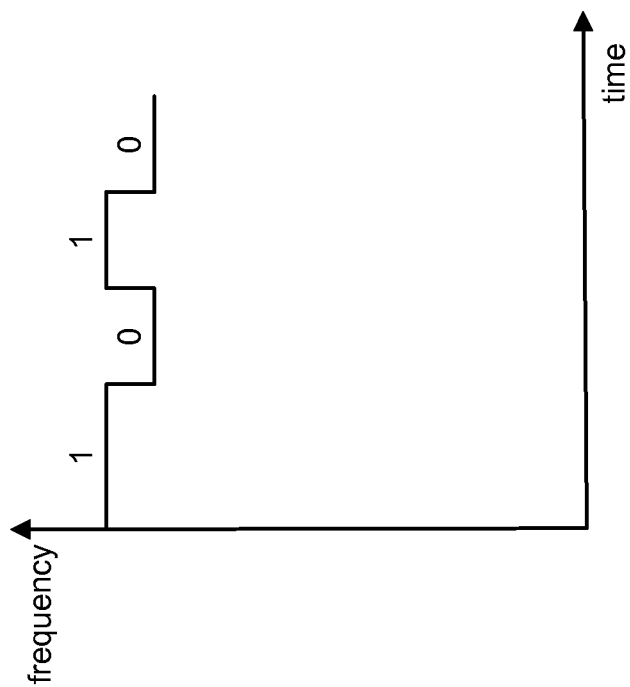

FIG. 1C illustrates one embodiment of encoding data into the operating frequency of the electric grid using a frequency "high" and frequency "low" to signify encoded binary data. Particularly, FIG. 1C illustrates a digital "1010" encoded into the operating frequency of the electric grid using an alternating pattern of low and high grid frequencies that respectively correspond to "0" and a "1" values. The encoded data may indicate geographical region(s) or types of electrical devices that are affected by the lower operating point of the electrical grid as previously mentioned above.

Although the encoding scheme illustrated in FIG. 1C is limited to basic alternating values of "0" and "1", it is useful in terms of preventing false triggering of load shedding devices. For example, a power plant going offline might cause a one-time change in grid frequency which would cause false triggering of load shedding devices. A grid operator may purposely encode the operating frequency to signify that the electric grid is reaching its maximum operating limits to prevent the false triggering.

FIG. 1D illustrates another embodiment of encoding data into the operating frequency of the electric grid where the duration of the frequency change encodes a specific binary value in the operating frequency. For example, a first duration of frequency change may be associated with a value of "1" whereas a second duration of frequency change may be associated with a value of "0". In FIG. 1D, the duration of $2\Delta t$ represents a value of "1" whereas the duration of $1\Delta t$ represents a value of "0". Accordingly, encoding of the operating frequency shown in FIG. 1D represents the value "1011". Although the encoding examples illustrated in FIG. 1C and FIG. 1D encode binary data into the operating frequency, note that trinary or other bit-depth data schemes may be used.

Figure 2:
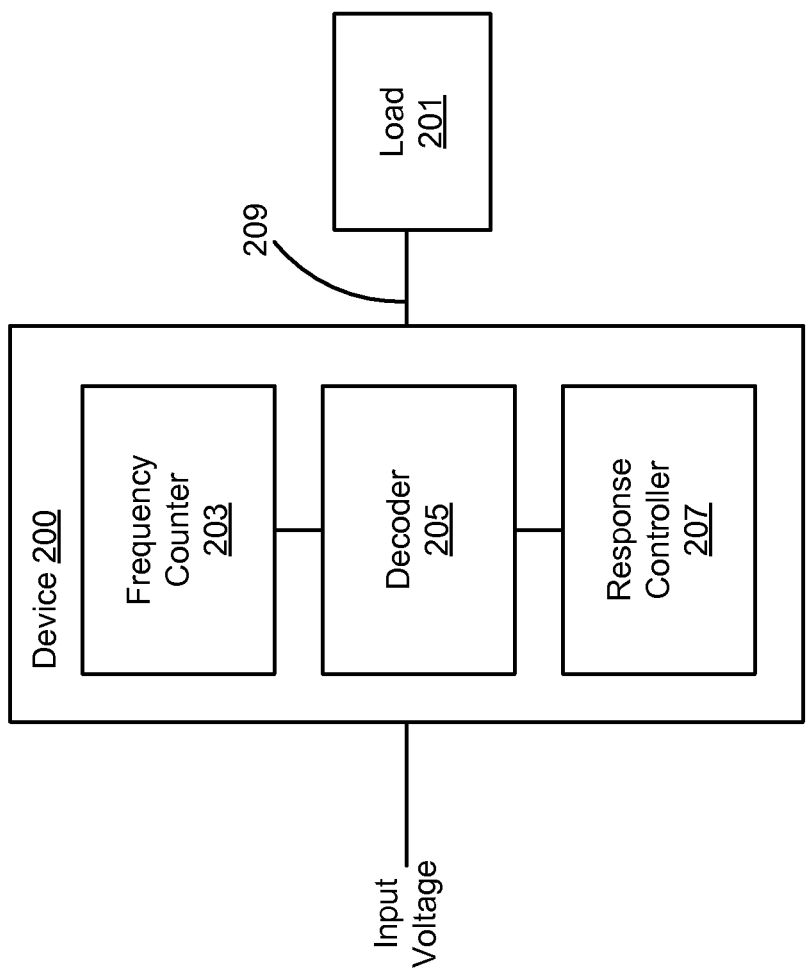
FIG. 2 is a block diagram illustrating a load shedding device that turns off a load, according to one embodiment.

FIG. 2 illustrates one embodiment of a load shedding device 200 that automatically turns off a load 201. In one embodiment, the device 200 may be coupled to the load 201 as shown in FIG. 2 or the device 200 may be incorporated into the load 201. Generally, the device 200 detects the lower operating frequency of the electric grid and the duration of the lower operating frequency from the input voltage being supplied to the device 200. The change in operating frequency and the duration of the change in operating frequency signifies that the electric grid is reaching maximum capacity. That is, the lower operating frequency of the electric grid and the duration of the change in operating frequency indicate to the device 200 that the grid reached the threshold percentage of the maximum load that it can support. In response to identifying the change in the operating frequency and the duration of the change in operating frequency, the device 200 signals (i.e., instructs) the load to turn off in order to reduce the demand on the electric grid.

In one embodiment, the device 200 comprises a frequency counter 203, a decoder 205, and a response controller 207. Note that in other embodiments, the device 200 may include other components other those illustrated in FIG. 2. As shown in FIG. 2, the device 200 receives an input voltage (e.g., 120 alternating current (AC) voltage) that is supplied by the electric grid. The frequency counter 203 measures the frequency of the input voltage and the duration of the measured frequency by counting the number of oscillations or pulses per second of the input voltage.

As mentioned previously, the operating frequency of the electric grid may be encoded with information indicating a geographical region and/or types of devices requiring energy conservation. In one embodiment, the decoder 205 decodes the information from the input voltage received by the device 200. For example, the decoder 205 may use Huffman decoding if the information was encoded using Huffman encoding. Specifically, the decoder 205 extracts the geographical region and/or device information encoded in the input voltage. The decoder 205 communicates the decoded information to the response controller 207.

The response controller 207 receives the measured frequency of the input voltage and the duration of the measured frequency from the frequency counter 203 and executes a response algorithm based on the measured frequency. In one embodiment, the response controller 207 may automatically turn off the load 201 in response to detecting that the measured frequency is below the threshold frequency for a threshold amount of time corresponding to when the electric grid is approaching maximum capacity. Specifically, the response controller 207 generates an instruction (i.e., a signal) 209 for the load 201 to turn off which is communicated to the load 201. Alternatively, the response controller 207 may provide an indication, such as a light indicator, that the electric grid is reaching its maximum capacity in response to detecting that the measured frequency is below the threshold frequency for a threshold amount of time. The owner of the load 201 may decide whether to turn off the load 201 or to allow the load 201 to continue to operate.

In one embodiment, the response controller 207 also receives the decoded information from decoder 205. The response controller 207 determines whether to turn off the load 201 based on the measured frequency and the decoded information. For example, the response controller 207 identifies the geographical location from the decoded information. As previously mentioned, the geographical location indicated in the decoded information indicates a location that is affected by the lower operating point of the electric grid. The response controller 207 determines whether the device 200 is located in the geographical location. In one embodiment, the device 200 may comprise a global positioning system (GPS) to identify the location of the device 200. Alternatively, the device 200 may detect a nearby Wi-Fi service set identifier (SSID) that names and identifies a wireless network. The device 200 may search a related database of WiFi locations associated with the SSID. In another embodiment, the device 200 may identify a zip code or postal code entered into the device 200 by the owner of the device 200.

In a further embodiment, the device 200 may be preprogrammed for a broad area, such as a city or state, and is shipped to distributors in those states assuming that the device 200 purchased at a given location will be installed within a threshold distance from where the device 200 was purchased. Thus, the response controller 207 determines the geographic location of the device 200 from the preprogrammed information. In another embodiment, the device 200 may include an FM or AM radio receiver that may be used to determine the geographic location from a specific channel such as a weather channel or an atomic clock channel.

If the load 201 is located at the geographical location, the response controller 207 instructs the load 201 to turn off in order to alleviate the demand on the electric grid. Alternatively, the response controller 207 may provide an indication (e.g. a light indication) that the electric grid is reaching its maximum capacity and allow the owner of the load 201 to decide whether to turn off the load 201 or to allow the load 201 to continue to operate.

The response controller 207 may also identify, from the decoded information, the types of devices that should be turned off in order to alleviate the demand on the electric grid. The response controller 207 determines whether the load 201 is the type of device (e.g., an air conditioner) specified in the decoded information. If the load 201 is the type of device specified in the decoded information, the response controller 207 instructs the load 201 to turn off or may provide an indication that the electric grid is reaching its maximum capacity. For example, if the device 200 is integrated into the load 201, the response controller 207 may be pre-programmed with a code corresponding to a device type (e.g., 0100) and may shut off if the code is indicated in the operating frequency.

Figure 3:
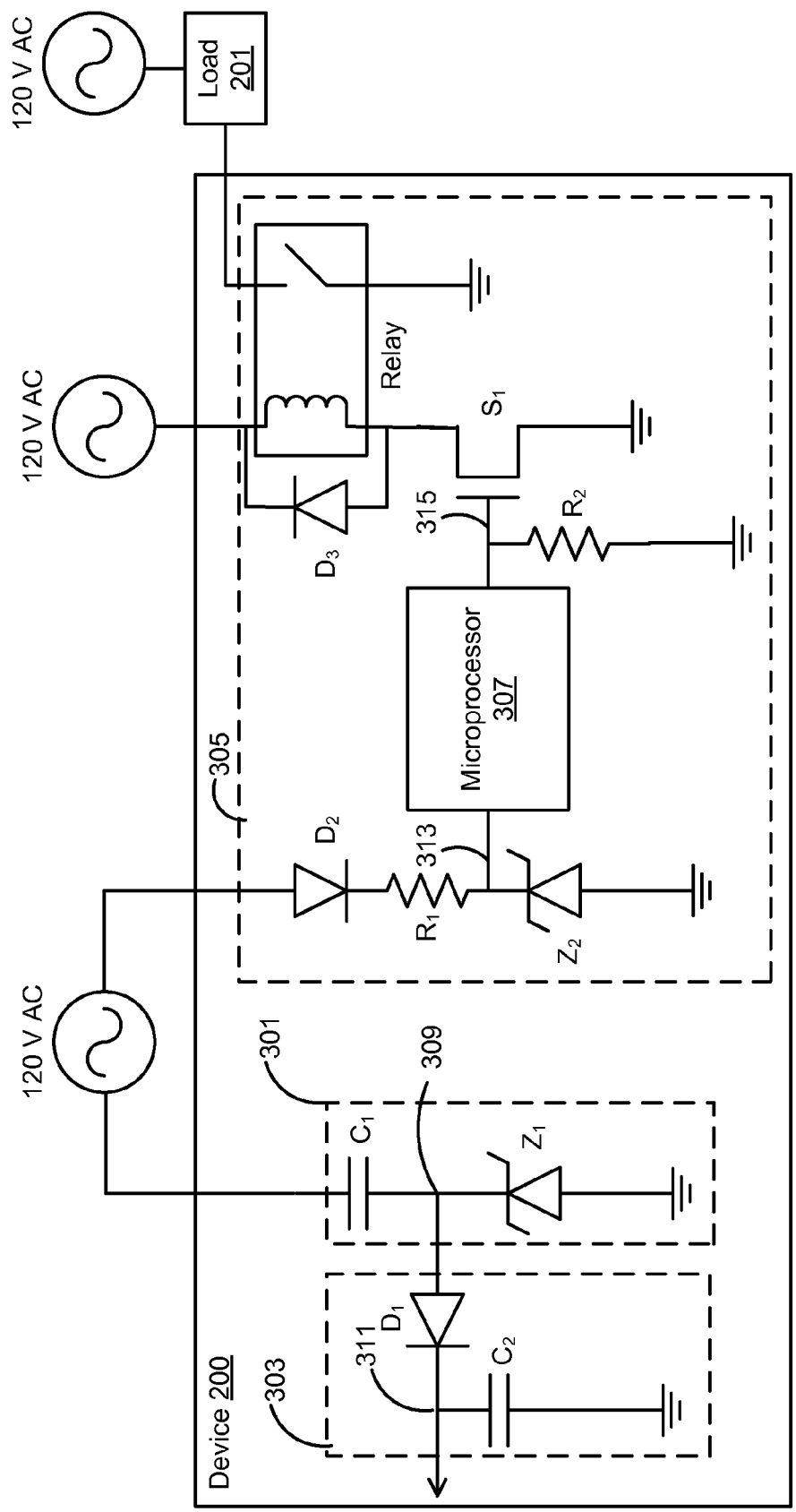
FIG. 3 is a circuit diagram illustrating the load shedding device shown in FIG. 2, according to one embodiment.

Referring now to FIG. 3, a detailed view of the load shedding device 200 is shown according to one embodiment. The device 200 comprises stage 301 that includes capacitor $C_1$ and a zener diode (e.g., a 3.9 V zener diode) $Z_1$. Stage 301 converts the 120 V AC input into an alternating voltage that alternates between 0V and 3.9 V in one embodiment. A 3.9 V drop occurs across the zener diode $Z_1$ thereby converting the 120 V AC into the alternating voltage between 0V and 3.9 V. More specifically, when the 120 V AC is above 3.9 V, the output 309 of stage 301 is 3.9 V. However, when the 120 V AC is below 3.9 V, the output 309 of stage 301 is 0 V.

Stage 303 comprises diode $D_1$ and capacitor $C_2$. Generally, stage 303 is a peak follower that outputs the peak voltage of the input. Stage 303 receives the alternating voltage output of stage 301 as its input and converts the alternating voltage into a steady direct current (DC) voltage. The diode $D_1$ conducts when the alternating input voltage is 3.9 V. The voltage drop across diode $D_1$ results in an output 311 of roughly 3.3 V. When the alternating input voltage drops to 0 V, the diode $D_1$ stops conducting and the capacitor $C_2$ maintains the 3.3 V at the output 311 of stage 303. The steady output voltage (e.g., 3.3 V) of stage 303 may be used to power the microprocessor 307 in one embodiment.

In one embodiment, stage 305 comprises diode $D_2$, resistor $R_1$, zener diode $Z_2$ (e.g., a 3 V zener diode), microprocessor 307, resistor $R_2$, a switch $S_1$, a diode $D_3$, and a relay. The combination of the diode $D_2$, resistor $R_1$, and zener diode $Z_2$ converts the 120 V AC into a digital signal that can be managed by the microprocessor 307. In one embodiment, the combination of the diode $D_2$, resistor $R_1$, and zener diode $Z_2$ outputs an oscillating voltage between 0V and 3 V. When the 120 V AC input voltage is above 3 V, diode $D_2$ conducts and the zener diode $Z_2$ holds the voltage at 3 V due to the 3 V voltage drop across the zener diode $Z_2$. When the 120 V AC input voltage is below 3V, the diode $D_2$ stops conducting and 0 V is inputted into the microprocessor 307. Thus, the combination of the diode $D_2$, resistor $R_1$, and zener diode $Z_2$ converts the 120 V AC into a digital signal that alternates between a 0 V and 3 V in the form of a square wave.

In one embodiment, the microprocessor 307 represents the frequency counter 203, the decoder 205, and the response controller 207 shown in FIG. 2. The microprocessor 307 receives as input 313 the digital signal resulting from the combination of the diode $D_2$, resistor $R_1$, and zener diode $Z_2$. The microprocessor 307 determines the frequency of the digital signal 313. In one embodiment, the microprocessor 307 samples the digital signal 313 and determines the frequency in which the digital signal alternates between 0 V and 3 V based on the samples of the digital signal 313. Responsive to the microprocessor 307 determining that the frequency of the digital signal 313 drops below the threshold frequency for a threshold amount of time, the microprocessor 307 causes the load 201 to turn off as will be further described below. Thus, the frequency of the digital signal 313 indicates to the microprocessor 307 to turn off the load 201 when the frequency is below the threshold frequency corresponding to when the electric grid is approaching its maximum capacity.

In one embodiment, the microprocessor 307 generates a signal 315 that is outputted to switch $S_1$. The signal generated by the microprocessor 307 turns on switch $S_1$ responsive to determining that the frequency of the digital signal drops below the threshold frequency for a threshold amount of time. The switch $S_1$ may be a metal-oxide-semiconductor field-effect transistor (MOSFET) in one embodiment. As shown in FIG. 3, the switch $S_1$ is coupled to a coil of the relay. When the switch $S_1$ turns on, current flows through the coil of the relay through the MOSFET to ground. In one embodiment, the relay is non-conducting (i.e., off) when the switch $S_1$ is on thereby disconnecting the load 201 (i.e., turning off the load). The diode $D_2$ placed across the coil of the relay dissipates energy from the magnetic field that is generated from the the current flowing through the coil of the relay.

Conversely, responsive to the microprocessor 307 determining that the frequency of the digital signal is above the threshold frequency, the microprocessor 307 allows the load 201 to stay turned on. Specifically, the microprocessor 307 outputs a signal 315 to turn off the switch $S_1$ responsive to the microprocessor 307 determining that the frequency of the digital signal 313 is above the threshold frequency. The current flowing through the coil of the relay generates a magnetic field that causes the relay to connect the load 201 to the device 200 thereby allowing the load 201 to stay turned on.

In one embodiment, the microprocessor 307 determines whether to turn on or turn off the load 201 based on information encoded in the digital signal 313 outputted from the combination of the diode $D_2$, resistor $R_1$, and zener diode $Z_2$. As previously mentioned, the information may specify a geographic region(s) and/or types of loads that need to be turned off when the electric grid approaches its maximum capacity. Responsive to the microprocessor 307 determining that the load 201 is located in a geographic region specified in the encoded information or is a type of device specified in the encoded information, the microprocessor 307 may turn off the load 201 upon detection that the frequency of the digital signal 313 drops below the threshold frequency corresponding to the electric grid approaching its maximum load.

In alternative embodiments where the load shedding device 200 is incorporated into the load 201, the microprocessor 307 may communicate with a controller of the load 201 to turn off the load 201. The microprocessor 307 may generate a signal instructing the controller of the load 201 to turn off the load 201 in response to the microprocessor 307 determining that the frequency of the digital signal drops below the threshold frequency.

Incentives

In one embodiment, people may be incentivized to purchase electrical devices that include the decentralized load shedding device 200 at a discounted price. Examples of the electrical devices that may incorporate the device 200 include air conditioners, televisions, washing machines, drying machines, hair dryers, or any type of power drawing electrical component. Thus, people may save money by purchasing an electronic device that automatically shuts down from time to time when the electric grid is approaching its maximum capacity rather than buying the same electrical device that can operate continuously until electricity is no longer supplied by the grid.

For example, a person may purchase an air conditioner at $100 that operates continuously or may opt to purchase the same air conditioner that includes the device 200 at $50. Thus, the person may accept that their air conditioner may shut off when the maximum load of the electric grid is approached in exchange for paying the lower purchase price. In one embodiment, governments may provide incentives to companies to produce electrical devices that include device 200. For example, the companies may benefit from a lower tax rate by producing electrical devices that include device 200.

In one embodiment, the device 200 may be incorporated into household electric meters. The device 200 may cause an electric meter to shut off thereby interrupting the electricity being supplied to the household when the electricity limits of the electric grid are being approached. The home owner may exchange the possibility of interruption of the electricity to his or her home for paying a lower rate for electricity thereby saving money.

Alternatively, utility companies may bill homeowners according to a variable rate based on time of day as well as the level of demand on the electric grid. Homeowners may receive a credit for reducing power usage when the grid is reaching maximum capacity due to having electrical devices that incorporate device 200 which shuts off electrical devices in the household when the grid is reaching maximum capacity. In one embodiment, the electrical meter may record a time stamped history of the electricity usage over the course of a month and at the end of the month, the utility company may correlate electricity usage with grid history. The utility company may bill homeowners appropriately by giving a discount to homeowners whose electricity usage dropped during periods in which the grid was reaching maximum capacity.

Reference in the specification to "one embodiment" or to "an embodiment" means that a particular feature, structure, or characteristic is included in at least one embodiment of the disclosure. The appearances of the phrase "in one embodiment" or "a preferred embodiment" in various places in the specification are not necessarily referring to the same embodiment.

Some portions of the above are presented in terms of methods and symbolic representations of operations on data bits within a computer memory. These descriptions and representations are the means used by those skilled in the art to most effectively convey the substance of their work to others skilled in the art. A method is here, and generally, conceived to be a self-consistent sequence of steps (instructions) leading to a desired result. The steps are those requiring physical manipulations of physical quantities. Usually, though not necessarily, these quantities take the form of electrical, magnetic or optical signals capable of being stored, transferred, combined, compared and otherwise manipulated. It is convenient at times, principally for reasons of common usage, to refer to these signals as bits, values, elements, symbols, characters, terms, numbers, or the like. Furthermore, it is also convenient at times, to refer to certain arrangements of steps requiring physical manipulations of physical quantities as modules or code devices, without loss of generality.

It should be borne in mind, however, that all of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "displaying" or "determining" or the like, refer to the action and processes of a computer system, or similar electronic computing device, that manipulates and transforms data represented as physical (electronic) quantities within the computer system memories or registers or other such information storage, transmission or display devices.

Certain aspects disclosed herein include process steps and instructions described herein in the form of a method. It should be noted that the process steps and instructions described herein can be embodied in software, firmware or hardware, and when embodied in software, can be downloaded to reside on and be operated from different platforms used by a variety of operating systems.

The embodiments discussed above also relates to an apparatus for performing the operations herein. This apparatus may be specially constructed for the required purposes, or it may comprise a general-purpose computer selectively activated or reconfigured by a computer program stored in the computer. Such a computer program may be stored in a non-transitory computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability.

The methods and displays presented herein are not inherently related to any particular computer or other apparatus. Various general-purpose systems may also be used with programs in accordance with the teachings herein, or it may prove convenient to construct more specialized apparatus to perform the required method steps. The required structure for a variety of these systems will appear from the description below. In addition, the embodiments are not described with reference to any particular programming language. It will be appreciated that a variety of programming languages may be used to implement the teachings described herein, and any references below to specific languages are provided for disclosure of enablement and best mode.

While the disclosure has been particularly shown and described with reference to a preferred embodiment and several alternate embodiments, it will be understood by persons skilled in the relevant art that various changes in form and details can be made therein without departing from the spirit and scope of the invention.

What is claimed is:

1. A decentralized load shedding device that automatically turns off a load, the device comprising:
a processor configured to:
determine an operating frequency of an electric grid;
determine that the operating frequency of the electrical grid has been lowered from a first operating frequency to a second operating frequency;
determine that the operating frequency of the electrical grid has been maintained at the second operating frequency for a threshold amount of time that indicates that the electrical grid is approaching operating point limits of the electrical grid;
in response to determining that the operating frequency has been lowered from the first operating frequency to the second operating frequency and maintained at the second operating frequency for the threshold amount of time, generate a signal for the load to turn off; and
send the generated signal to the load to cause the load to turn off;
wherein the operating frequency of the electrical grid is lowered to the second operating frequency and maintained at the second operating frequency before the electrical grid is at the operating point limit of the electrical grid; and
wherein the operating frequency is encoded with information describing a geographic location that is affected by the electric grid approaching the operating point limits of the electric grid and wherein the processor generates the signal responsive to the load being located in the geographical location.

2. The device of claim 1, wherein the device is incorporated into the load.

3. The device of claim 1, wherein the device is coupled to the load.

4. The device of claim 1, wherein the load comprises an electric appliance.

5. The device of claim 1, wherein the processor is further configured to determine the operating frequency of the electric grid from an input voltage to the device.

6. The device of claim 1, wherein the operating frequency is encoded with information describing a type of device that is affected by the electric grid approaching the operating point limits of the electric grid and wherein the processor generates the signal responsive to the load being the type of device encoded in the operating frequency.

7. A method of operating a decentralized load shedding device that automatically turns off a load, the method executed by the device and comprising:
determining an operating frequency of an electric grid;
determining that the operating frequency of the electrical grid has been lowered from a first operating frequency to a second operating frequency;
determining that the operating frequency of the electrical grid has been maintained at the second operating frequency for a threshold amount of time;
in response to determining that the operating frequency has been lowered from the first operating frequency to the second operating frequency and maintained at the second operating frequency for the threshold amount of time that indicates that the electrical grid is approaching operating point limits of the electrical grid, generating a signal for the load to turn off;
sending the generated signal to the load to cause the load to turn off;
wherein the operating frequency of the electrical grid is lowered to the second operating frequency and maintained at the second operating frequency before the electrical grid is at the operating point limit of the electrical grid; and
wherein the operating frequency is encoded with information describing a geographic location that is affected by the electric grid approaching the operating point limits of the electric grid and the method further comprises:
generating the signal responsive to the load being located in the geographical location.

8. The method of claim 7, wherein determining the operating frequency of the electric grid comprises:
determining the operating frequency of the electric grid from an input voltage to the device.

9. The method of claim 7, wherein determining the operating frequency of the electric grid comprises:
determining that the operating frequency lowered from a first operating frequency to a second operating frequency that is below a threshold frequency for a threshold amount of time, the threshold frequency and the threshold amount of time indicating that the electric grid is approaching the operating point limits of the electric grid.

10. The method of claim 7, wherein the operating frequency is encoded with information describing a type of device that is affected by the electric grid approaching the operating point limits of the electric grid and the method further comprises:
generating the signal responsive to the load being the type of device encoded in the operating frequency.

* * * * *